US005538722A

United States Patent [19]

Blau et al.

[11] Patent Number: 5,538,722
[45] Date of Patent: Jul. 23, 1996

[54] ISOLATION, GROWTH, DIFFERENTIATION AND GENETIC ENGINEERING OF HUMAN MUSCLE CELLS

[75] Inventors: Helen M. Blau, Menlo Park; Simon M. Hughes, Palo Alto, both of Calif.

[73] Assignee: Stanford University, Stanford, Calif.

[21] Appl. No.: 748,348

[22] Filed: Aug. 22, 1991

Related U.S. Application Data

[63] Continuation-in-part of Ser. No. 365,374, Jun. 13, 1989, abandoned.
[51] Int. Cl.⁶ ............................. A61K 48/00; C12N 15/00
[52] U.S. Cl. ................. 424/93.21; 435/69.4; 435/240.2; 435/172.3
[58] Field of Search ............................ 424/93 B, 93 U; 435/240.2, 172.3, 69.4; 935/62, 70, 71

[56] References Cited

PUBLICATIONS

Partridge, Muscle & Nerve, vol. 14 pp. 197–212 (Mar. 1991)
Partridge, J. Cellular Biochem., Supp. 14E p. 233 (Mar. Apr. 1990).
Law et al, Muscle & Nerve, vol. 11, pp. 525–533 (Jun. 1988).
Melloul et al, EMBO J. vol. 3, No. 5 pp. 983–990 (1984).
Selden et al., Science, vol. 236, pp. 714–718 (8 May 1987).

*Primary Examiner*—Jacqueline M. Stone
*Attorney, Agent, or Firm*—Bertram I. Rowland

[57] ABSTRACT

Myoblasts are produced, conveniently in low or serum-free medium, for use in introduction into a mammalian host, particularly a human host, for treatment of diseases of muscle tissue or acting as carriers for genetic capabilities, particularly correcting a genetic defect or for production of a soluble protein, which may serve in a therapy for the mammalian host. Myoblasts introduced into tissue are able to migrate to sites distal from the site of injection, expanding the area of their effect.

4 Claims, 2 Drawing Sheets

ISOLATION, GROWTH, DIFFERENTIATION AND GENETIC ENGINEERING OF HUMAN MUSCLE CELLS

CROSS-REFERENCE TO RELATED APPLICATIONS

This application is a continuation-in-part of application Ser. No. 07/365,374, filed Jun. 13, 1989, now abandoned.

INTRODUCTION

1. Technical Field

The field of this invention is the development of myoblasts for use in the treatment of neuromuscular disease and for genetic engineering for cellular therapy of diseases or conditions of diverse etiology.

2. Background

Myoblasts are precursor cells of the mesoderm that are destined for myogenesis. The determined myoblasts are capable of recognizing and spontaneously fusing with other myoblasts leading to the production of a differentiated myotube. The multinucleated myotube no longer divides or synthesizes DNA but produces muscle proteins in large quantity. These include constituents of the contractile apparatus and specialized cell-surface components essential to neuromuscular transmission. Eventually, the differentiated muscle cell exhibits characteristic striations and rhythmic contractions. A further step in this pathway is maturation; the contractile apparatus and muscle at different stages of development contain distinct isoforms of muscle proteins such as myosin and actin, encoded by different members of multigene families.

Methods have been developed for production of myoblasts from fetal and adult tissue. The success of these methods suggests that it is possible to generate large volumes of myoblasts from adult muscle tissue that are substantially free of other cells. There is, therefore, substantial interest in developing ways in which the myoblasts may be used for therapeutic purposes and to understand the etiology of diseases affecting muscle tissue. The myoblasts have the potential for being used in a variety of ways. First, the myoblasts may serve as cell therapy for the treatment of various diseases associated with genetic or nongenetic defects involving muscle tissue. The myoblasts may also be useful as vehicles for gene therapy, where one or more genes may be introduced into the myoblasts to provide a product of interest. These genes may be muscle genes or non-muscle genes for the treatment of muscle or non-muscle diseases or for providing novel or enhanced genetic capabilities.

RELEVANT LITERATURE

Blau, H. M. and Webster C., (1981) *Proc. Natl. Acad. Sci. USA* 78:5623–5627 describe isolation and cloning of human muscle cells for proliferation or differentiation of individual clones. Blau et al., (1983) *Proc. Natl. Acad. Sci. USA* 80:4856–4860 describe a defect in proliferative capacity specific to myoblasts (satellite cells), mononucleated precursors of mature muscle fibers, in clonal analyses of cells cultured from Duchenne muscular dystrophy patients; fibroblasts from the same muscle tissues have normal proliferative capacity. Blau et al., (1982) *Life Sci.* 32:45–53 describe the use of human extraocular myoblasts obtained post mortem at autopsy in studies of cell mediated cytotoxicity of autoimmune diseases such as Grave's disease. Blau et al., (1983) *Exp. Cell Res.* 144:495–503 describe the production and analyze the properties of pure myoblast clones from biopsies of patients with Duchenne muscular dystrophy. Blau et al., (1985) *Science* 230: 758–766 describe the fusion of muscle cells with non-muscle cells with activation of human muscle gene expression in a number of normal human non-muscle cell types. Webster et al., (1986) *Human Genetics* 74:74–80 determine that the proliferative defect of Duchenne myoblasts is not a primary expression of the DMD mutation; instead it is secondary to the exhaustion of cell doublings as the myoblasts attempt to regenerate degenerating muscle fibers. Kaplan and Blau (1986) *Exp Cell Res* 166:379–390 describe the use of myoblasts obtained from a 70 year old at autopsy to characterize the metabolic properties of human acetylcholine receptors. Costa et al., (1986) *Endocrinology* 119(5):2214–2220 and Shimizu et al., (1986) *Amer. J. Physiol.* 251:E611–E615 describe receptors and responses of cultured human muscle cells to 1,25-dihydroxyvitamin $D_3$ and to insulin and insulin-like growth factor, respectively. Gunning et al., (1987) *Mol. Cell. Biol.* 7:4100–4114 describe the differential patterns of myogenic transcript accumulation in differentiating human myoblasts. Miller et al., (1988) *Mol. Cell. Biol.* 8:2295–2301 describe the inhibition of human myoblast differentiation by tumor necrosis factor. Webster et al., (1988) *Exp. Cell Res.* 174: 252–265 describe the purification of human myoblasts using a fluorescence activated cell sorter. Ham et al., (1988) *In Vitro Cell. & Dev. Biol* 24:833–844 describe a serum-free medium for clonal growth of human muscle satellite cells. Webster et al., (1988) *Cell* 52:503–513, describe a subset of skeletal muscle fibers specialized for fast contraction that are the first fibers to degenerate in Duchenne muscular dystrophy (see also the references cited therein). Kaplan et al., (1990) *Proc. Natl. Acad. Sci. U.S.A.* 87:8100–8104 describe effects of steroids in augmenting acetylcholine receptors on human muscle cells and their physiologic and therapeutic implications for patients with the autoimmune disorder, myasthenia gravis. Hughes and Blau, (1990) *Nature* 345:350–353 describe the migration of genetically engineered myoblasts across basal lamina. Webster and Blau, (1990) *Soma. Cell and Mol. Gen.* 16:557–565 describe the large number of cells that can be obtained per myoblast from a normal donor: 30 to 60 doublings or as many as $10^{18}$ cells/cell depending on age of normal muscle donor; by contrast, myoblasts from Duchenne patients exhibit an age-related decline in replicative lifespan which is greatly accelerated indicating that only myoblasts from very young patients could be genetically engineered. Schaefer et al., (1990) *Nature* 344:454–458 show that human fibroblasts can be heritably converted to myoblasts that express muscle genes and have a distribution of organelles typical of muscle by introducing the MyoD gene by stable transfection or retroviral infection. Montegazza et al., (1991) *Neurobiology* 41:1128–1132, show that MHC class II antigen expression is induced in human myoblasts by treatment with gamma interferon.

SUMMARY OF THE INVENTION

Myoblast cells and methods of use are provided, which cells may be grown in culture, purified by cloning or with a flow cytometer (FACS), and may be used for cell therapy, either as wild type cells or genetically modified cells.

The myoblasts are capable of migrating, particularly to sites of injury, fusing into pre-existing fibers, and may serve as carriers for genes, which may correct genetic defects, supply surface membrane proteins or secreted products, or allow for the elucidation of mechanisms involving the development of muscle. The myoblasts migrate across basal lamina, so that with only a few injections, a relatively large area may be treated.

DESCRIPTION OF THE SPECIFIC EMBODIMENTS

Methods and cells are provided for use in cellular therapies for the treatment of diseases or to provide a source of proteins, and the like. Methods are described for preparing clonally pure or substantially enriched myoblasts in large amounts in the absence or substantial absence of serum in the nutrient medium. The resulting cells may be used for treatment of a variety of diseases associated with muscle tissue, or production of products, particularly for the treatment of other tissues where a soluble factor is involved.

The cells which are employed are normal myoblasts, which may be obtained from tissue samples, which may include fetuses, neonates or tissue from older humans, obtained live or at autopsy. These cells may be used fresh, maintained as tissues on ice for several days, or dissociated and plated in culture for one week and then frozen. They may be clonal cultures of pure myoblasts which are grown up from about 5 up to about and usually not greater than about 60 population doublings, or substantially enriched myoblasts purified with a cell sorter and then stored frozen for use. For some purposes, permanent mouse myogenic cell lines of unlimited lifespan may be employed experimentally, which cell lines have some characteristics of neoplastic cells. However, the cells isolated from normal human muscle tissue and used therapeutically are karyotypically stable and have limited lifespan and will not be neoplastic.

Pure (99%) populations of human myoblasts can be obtained in quantity, stored frozen and used in replicate experiments or clinical trials as needed. These methods for isolation and growth of human myoblasts can be applied to diverse muscles such as limb, trunk and extra-ocular; to diverse stages of development including fetal, newborn and adult up to at least 70 years; to dystrophic tissue including Duchenne and Becker muscular dystrophy, dermatomyositis, spinal muscular atrophy I and II and denervation atrophy; tissue 7 days post biopsy in saline at 4° C.; and tissue post mortem at autopsy. Thus, human myoblasts are hardy, tissue sources, can be readily shipped, and a universal donor source could be obtained after death. Duchenne myoblasts have limited proliferative capacity and cannot be readily engineered genetically except when obtained from patients of very young ages. However, Duchenne fibroblasts retain their proliferative capacity even when obtained from patients at advanced ages and could be converted to myoblasts with MyoD or myogenin and then genetically engineered with the dystrophin gene. Genetically engineered myoblasts cross basal lamina in normal development or following injection into muscle tissue and fuse into mature muscle fibers.

Growth and Purification of Myoblasts

The cells are grown in the subject media in a cell culture incubator (37° C., 5% $CO_2$ in air, saturated humidity), as the optimal conditions. Other conditions may be employed, if desired. The chosen medium provides for proliferation, without significant differentiation. Thus, the medium retains the myoblast level of maturation and, when desired, the myoblasts may be introduced into an environment, where they will differentiate and mature.

To grow the myoblasts, an inoculum is introduced into an appropriate medium and the cells grown under the conditions indicated above. After adding the inoculum, mild agitation may be employed to ensure uniform distribution of the cells for growth as undifferentiated cells at low density.

Cells may be harvested in any convenient way. Tissue may be dissociated for a total of 40–60 min by two or three successive treatments with 0.05% trypsin—EDTA at 37° C. in a Wheaton graduated trypsinization flask with constant stirring. The cells collected in the supernatant after each trypsin treatment are pooled and cooled to 4° C. on ice. Calf serum is added to a final concentration of 10% (vol/vol) to terminate further protease activity. The dissociated cells are then centrifuged (2 min, 25° C.); the cell pellet is resuspended in conditioned media (media collected from cultures of confluent human fibroblasts after 24 h, filtered 0.45 μm, and diluted 1:1 with fresh media) and either plated in culture or frozen in liquid nitrogen at a density of about 0.1 $cm^3$ of tissue per ml. Cell yield is increased if cells are grown in culture for several days prior to freezing.

Myoblasts can be enriched using a fluorescence activated cell sorter after labeling with a monoclonal antibody to muscle NCAM (5.1H11) followed either by a second fluorescein conjugated antibody or a three-step Texas red avidin labeling procedure. (In the three-step procedure, one uses the specific antibody to the NCAM, a second antimouse IgG that is biotinylated, and Texas red avidin which provides for a large amplification of signal.) Myoblasts which comprise as little as 24% of the total cells are enriched to greater than 99% purity and this enrichment is maintained for up to a month in culture.

If myoblasts cannot be obtained in quantity, for example in the case of muscle tissue from Duchenne muscular dystrophy patients, then fibroblasts from the same tissue that have normal proliferative capacity can be used in their place. Human fibroblasts may be converted heritably to myoblasts that express muscle genes and have a muscle cytoarchitecture: muscle distribution of organelles such as the Golgi apparatus, microtubule organizing center, and centrioles. This is achieved by expression of the endogenous gene (homologous recombinaton with a constitutive promoter) or an introduced gene encoding MyoD or myogenin or another member of this gene family for constitutive expression. Such genetically engineered "myoblasts" may serve in place of true myoblasts in all of the manipulations described below.

Universal donor myoblasts

Desirably, the cells will be major histocompatibility complex MHC antigen matched, either by being autologous or heterologous from a person having the same or similar MHC antigen profile, or the patient tolerized to the allogeneic MHC antigens. On the other hand, it may be possible to achieve the same end and circumvent this type of individualized therapy by producing cells that lack MHC Class I and/or II. In this approach cells from a single donor, a "universal donor" could be used for treatment of multiple patients. Class I negative cells may be achieved by interfering with expression and\or transport of the alpha-chain, while Class II negative cells will require interference with expression and\or transport of both alpha and beta chains.

Inactivation of the Class I and/or Class II MHC antigens can be achieved in a variety of ways. For example, with Class I, one may overexpress a single modified $B_2$-microglobulin gene whose protein product effectively complexes with Class I MHC molecules and acts as a decoy preventing the insertion of the Class I MHC antigens in the membrane. A similar "dominant negative" approach could be used for Class II by overexpressing modified genes encoding defective $\alpha$ or $\beta$ subunits that complex with the host cells' subunits rendering them nonfunctional. Expression of modified MHC or $\beta_2$ microglobulin genes or inactivation of genes may be achieved either by transfection, retroviral infection or homologous recombination.

Alternatively, levels of Class I antigens on the cell surface can be reduced by introducing into myoblasts a sequence encoding adenoviral E19 protein by transfection or retroviral infection. This protein forms complexes specifically with MHC class I antigens in the rough endoplasmic reticulum preventing normal transport of Class I molecules to the plasma membrane (Andersson et al., (1985) *Cell* 43:215–222; for a review see Pabo et al., (1989) *Advances in Cancer Research* 52:151–163). No proteins other than Class I and E19 molecules appear to be involved in these complexes. Within 18 hr of expression, Class I expression may be reduced by 70%. E19 protein diminishes the ability of cytotoxic T lymphocytes to recognize cells. In contrast to other adenovirus proteins, E19 is not tumorigenic. The cells engineered with the E19 gene, like virally infected cells, may escape immune surveillance.

Genetic engineering of myoblasts

In culture, the myoblasts may be genetically engineered in any of a wide variety of ways, including fusion, transfection, lipofection, infection, electroporation, biolistics with DNA coated particles, or the like. The particular method for introducing the foreign DNA is not crucial to this invention. Depending on the purpose for the introduction of the DNA, there may be an interest in having directed homologous (legitimate integration) recombination or illegitimate recombination.: see Smithies, et al., (1985) *Nature* 317:230–235; Thomas and Capecchi (1987) *Cell* 51:503–512 and Mansour, et al., (1988) *Nature* 336:348–352. For directed integration, the gene of interest will usually be flanked by at least about 10 bp, frequently 50 bp, on at least one side with DNA homologous to the site for integration, usually at least 100 bp, and the total of homologous DNA of interest may be as high as 10 kbp, usually not greater than about 5 kbp, where preferably the flanking regions will be of about the same size.

Various techniques may be employed for directed integration, or homologous recombination, to ensure that the targeted genes have been inactivated or modified. Expressed genes have been inactivated or mutated at a frequency of 70–85% by homologous recombination when the promoter of the target gene remains active and the fusion protein produced allows for selection with G418, hygromycin, the fluorescence activated cell sorter or the like (Riele et al., (1990) *Nature* 348:649–651; Jasin et al., (1990) *Genes and Dev.* 4:157–166).

Regions for integration may include DNA sequences associated with a particular muscular defect. Thus, the host myoblasts may be removed from the host, genetically engineered by homologous recombination, and cells cloned and screened for homologous recombination at the site of the defect. Alternatively, where a naturally occurring inducible gene is involved, which is normally suppressed in a myoblast or mature muscle tissue, one may provide for homologous recombination, where the transcriptional initiation regulatory sequence, e.g., promoter with or without an enhancer, is modified to provide for a different basis for induction or for constitutive transcription. Thus, the myoblasts may be used for expression of an endogenous gene (native to the host) or heterologous, which is normally not expressed in muscle tissue. For example, one may wish to provide for expression of cytokines, growth factors, (e.g., EGF, FGF, etc.), colony stimulating factors, interferons, surface membrane receptors, insulin or the like. By modifying the transcriptional initiation regulatory region, the myoblasts may provide for constitutive production of the expression product or, alternatively or in combination, one may introduce a receptor for the soluble product, which provides for inducible transcription of a cellular, e.g., cytoplasmic, nuclear, etc., protein. By activating the receptor, the myoblasts may be induced to produce the expression product under the induction of the relevant ligand.

Various regulatory regions may be employed for transcriptional initiation, where the regions may be native and transcriptionally active in the myoblasts or may be heterologous or may be associated with genes which are not expressed in muscle cells, myoblasts and myotubes. The initiation regions will usually be strong promoters and may include enhancers which are active in muscle cells. Promoters of interest include the beta-actin promoter, the alpha-actin promoter, tubulin promoter, myosin promoter, promoters of viruses, such as Simian virus, adenovirus, papilloma virus, cystomegalovirus etc.

Various vehicles or vector constructs may be employed for the genetic engineering of the myoblast cells. Of particular interest for transfection or infection are replication-defective viral vectors, DNA virus or retroviral (RNA) vectors, which may be introduced into the cells. The vectors will normally be substantially free of any prokaryotic DNA and may comprise a number of different functional sequences. As already discussed, one of the functional sequences may be a DNA region comprising transcriptional and translational initiation and termination regulatory sequences, an open reading frame encoding the protein of interest, and may further comprise flanking regions for site directed integration. In some situations, as already indicated, the 5'-flanking region will provide for homologous recombination to change the nature of the transcriptional initiation region. For example, the presence or absence of an enhancer may be modified, to provide for inducible transcription or noninducible transcription, to increase or decrease the level of transcription, or the like. Similarly, the promoter region may be modified, so as to be more or less susceptible to induction, to increase or decrease the level of transcription, or the like.

The structural gene which is employed may result in an intracellular product, i.e., retained in the cell, in the cytoplasm or organelle, e.g., the nucleus, in transport to a membrane, either an intracellular membrane or the cell membrane, or for secretion by providing for the natural signal sequence present within the structural gene or a signal sequence which is not naturally present within the structural gene. In some situations, where the soluble protein of interest is a fragment of a larger protein, it may be necessary to provide a signal sequence with such protein, so that upon secretion and processing at the processing site, the desired protein will have the natural sequence. Examples might include growth hormone, Factor VIII, Factor IX, cytokines, angiogenic factors to promote cardiac vascularization, antagonists of cytokine receptors, glucose transporters, insulin receptors, contraceptives, or addressins to promote adhesion and migration to specific sites. The following table indicates various genes of interest and associated diseases as appropriate:

Targets for gene therapy

1. Single gene defects:

Factor IX and Factor VIII (hemophilias: clotting disorders)

alpha-1-antitrypsin (emphysema)

growth hormone (inherited and acquired growth hormone deficiency)

other hormone deficiencies adenosine deaminase (other immunodeficiency disorders)

enzyme defects (metabolic disorders)

dystrophin (Duchenne and Becker muscular dystrophy)

2. Cancer:

interferon (leukemia)

Interleukin-2 (T-cell activator: leads to tumor shrinkage)

leuprolide:analog of human gonadotropin (ovarian and testicular)

asparaginase (leukemia)

monoclonal antibodies (specific IgG) to specific proteins surface of tumor cells including chimeric mouse human antibodies granulocyte colony stimulating factor (all cancers: allows higher doses of chemotherapy 3. Brain:

if access to brain is possible: implanting muscle in brain glucocerebrosidase (other lysosomal storage disorders; Tay Sachs)

Levodopa (Parkinson's)

nerve growth factor (Alzheimer's)

some neurotransmitter disorders other gene products and metabolites useful in the treatment of genetic, developmental, degenerative, traumatic, or infectious, kinds of dysfunction of the mammalian CNS 4. If regulated expression is achieved:

insulin (diabetes)

glucose transporter (diabetes)

growth factors: IGF-I and IGF-II

5. Infectious diseases:

delivery of antisense sequences, toxin genes, or other genes into cells to interfere with expression of the pathogenic genetic functions 6. Contraception:

antibody to human chorionic gonadotropin antibodies to zona pellucida antigens or sperm antigens RU-486 progesterone antagonist 7. Pain:

endorphins (dynorphin): endogenous opiates

8. Clotting disorders:

Factor VIII and Factor IX (hemophilias)

tissue plasminogen activator

9. Organ and cell transplants:

antibody to CD4 (HLA)

10. AIDS:

growth hormone to stimulate lymphocyte proliferation

CD4 protein as a decoy to keep virus from interacting with CD4+ cells

11. Other:

hormones, serum proteins, other humoral or diffusible proteins, and low molecular weight metabolic products A marker may be present for selection of cells which contain the vehicle construct. Normally, the marker will allow for positive selection, in providing protection from one or more cytotoxic agents. For example, neomycin resistance may be employed, where the cells may be selected with G418, dihydrofolate reductase may be employed for resistance to methotrexate, the cell sorter may be used to select cells expressing LacZ, and the like. The marker may be an inducible or non-inducible gene, so that selection may occur under induction or without induction.

The vector may also include a replication origin and such other genes which are necessary for replication in the host. The replication system comprising the origin and any proteins associated with replication encoded by the particular virus may be included as part of a construct. Care must be taken in selecting the replication system, so that the genes which are encoded for replication do not provide for transformation of the myoblasts. Illustrative replication systems include Epstein-Barr virus (Margolskee et al., (1988) *Mol. Cell. Biol.* 8:2837–2847). Alternatively, replication defective vehicles may be employed, particularly replication-defective retroviral vectors. These vectors are described by Price et al., (1987) *Proc. Natl. Acad. Sci.* 84:156–160 and Sanes, et al., (1986) *EMBO J.* 5:3133–3142. The final vehicle construct may have one or more genes of interest. Either a cDNA gene or a chromosomal gene may be employed.

Alternatively, cells may be genetically engineered in vivo by injection of replication-defective viral vectors, which are infectious. The vectors may be introduced into retro-viral producer cells for amphotropic packaging. The virus is then collected, filtered and concentrated by centrifugation and the viral stock may then be injected into a site in vivo. Since it is found that the myoblasts will migrate, relatively few injections at the site of interest into the muscle fibers are required, since the myoblasts will expand into adjacent regions.

Myoblast migration allows access to damaged sites

The myoblasts are found to migrate from the original site of injection to other sites, particularly injured sites, e.g., degenerating foci. It thus appears that there is a homing phenomenon which permits the treatment of injured sites by injecting myoblasts into the host, particularly in tissue, usually muscle tissue, proximal to the injuries, although injection into the circulation may also be possible. By employing genetically engineered myoblasts one may provide for directed application of soluble protein products to the injured regions, without having to inject the myoblasts at the injured region. The homing of the myoblasts to the injured tissue opens up new therapeutic avenues for treatment of muscle injury.

Depending upon the agent employed for modification of the muscle tissue, either myoblasts or the replication-defective viral vectors, the mode of administration may differ. For cells, usually the injections will be about $10^5$ to $10^6$ cells per $cm^3$ of muscle tissue to be treated. For the viral vector, the concentration will depend on the application. The vector will be conveniently administered by injection in a physiologically acceptable medium, such as saline, phosphate buffered saline, or the like. Other additives which may be present include polybrene.

The trauma to the tissue is substantially minimized by having relatively few injections in the region of interest. Particularly, where the patient may have need for extensive treatment, the desirability of having a low number of injections in a particular area is manifest.

The following examples are offered by way of illustration and not by way of limitation.

EXPERIMENTAL

A. VECTORS

Introduction of genes (LacZ) by retroviral infection of muscle tissues.

1) BAG (Price et al., (1987) *Proc. Natl. Acad. Sci. USA* 84:156–160) is a retrovirus that expresses the *E.coli* LacZ gene (encoding β-galactosidase) under the transcriptional control of the Moloney murine leukemia virus long terminal repeat (MMuLV 5'LTR) and gag pr65 translation initiation codon, and the neomycin resistance gene under the control of the SV40 early promoter.

(2) MMuLVSVnlsLacZ (Bonnerot et al., (1987) *Proc. Natl. Acad. Sci. USA* 84:6795–6799) is a retrovirus that expresses a modified *E.coli* LacZ gene (encoding β-galactosidase) onto which the 10 amino acid nuclear localization signal of SV40 T antigen was engineered at the N-terminus. The LacZ gene is embedded within Moloney murine leukemia virus 5' and 3' long terminal repeats and is under the control of the SV40 early promoter.

The BAG and MMuLVSVnlsLacZ retroviruses were generously provided by Drs. Cepko (Harvard U.) and Nicolas (Institut Pasteur), respectively. For infection, supernatant from CREBAG2 retroviral producer cells was obtained following transfection of BAG into the ψCRE packaging cell line that is recombination resistant (Danos and Mulligan (1988) *Proc. Natl. Acad. Sci. USA* 85:6460–6464) filtered and concentrated. The MMuLVSVnlsLacZ vector was produced by transfection of MMuLVSVnlsLacZ into the ψ2 packaging cell line (Bonnerot et al., (1987), op. cit.).

Introduction of genes (LacZ, hGH, and adeno E19) by retroviral infection of myogenic cells in culture which were subsequently injected into muscle tissue.

Figure 1:
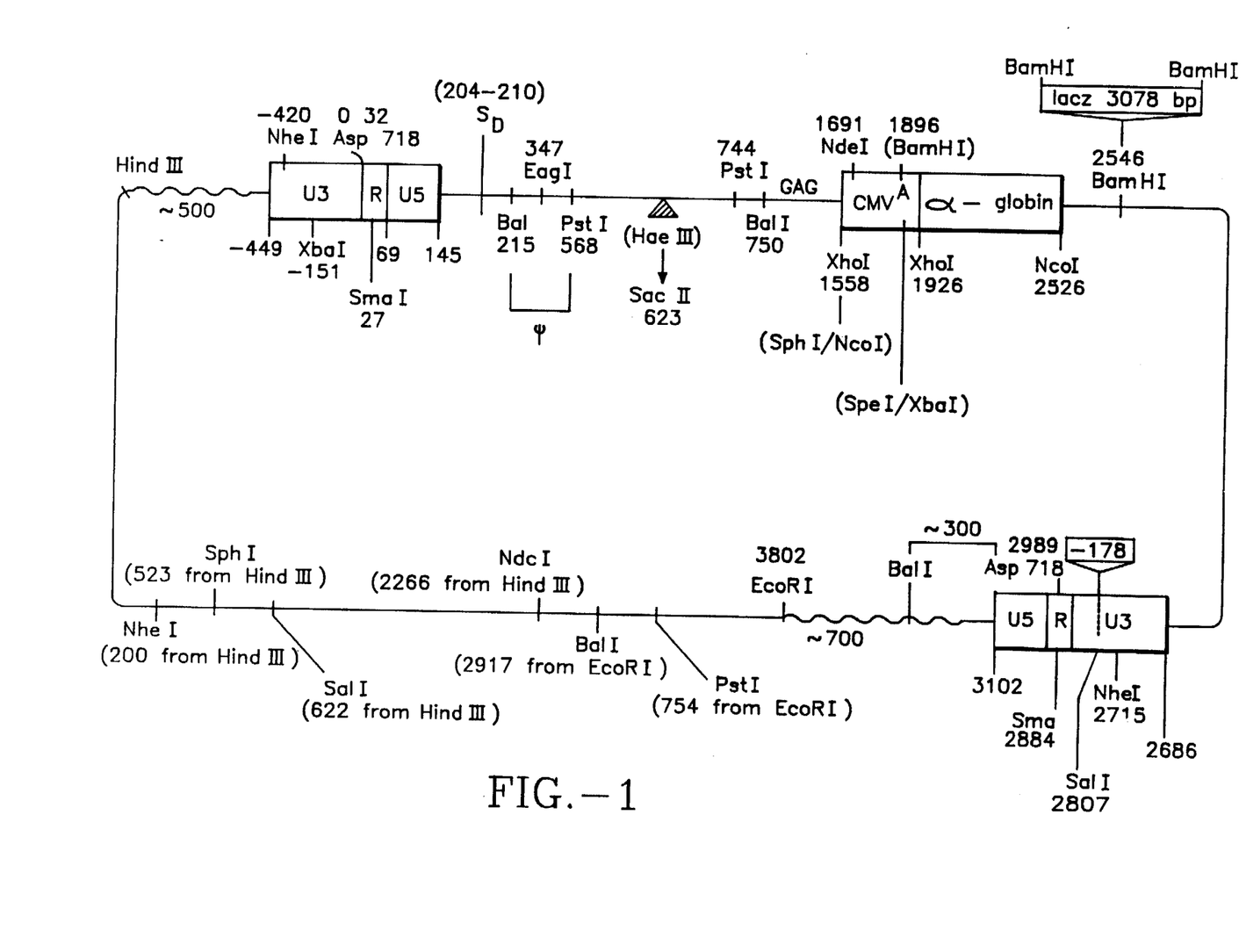
FIG. 1 is a map of the retroviral vector α-SGC.

(5) α-SGC (See FIG. 1) is a retrovirus referred to as self-inactivating that expresses the *E. coli* LacZ gene under the control of the CMV enhancer and α-globin basal promoter. High level lacZ expression from the internal promoter is made possible by a deletion in the viral 3'LTR resulting in a transcriptionally disabled 5'LTR following infection of cells. The producer cell line (3T3 mouse cell line) for this vector is ψCRIP and known as α38. Cone et al., Science 236, 954 (1987); Danos and Mulligan, Proc. Natl. Acad. Sci. USA 85, 6460 (1988) The advantages of this construct are:

(a) the reduced probability of insertional mutagenesis caused by activation of endogenous genes at the proviral insertion site by the control elements of the LTR; and (b) the reduced likelihood of packaging viral RNA into infective virus particles by endogenous retroviruses in infected cells, because a functional 5'LTR and ψ packaging signal are absent from the viral transcripts.

Figure 2:
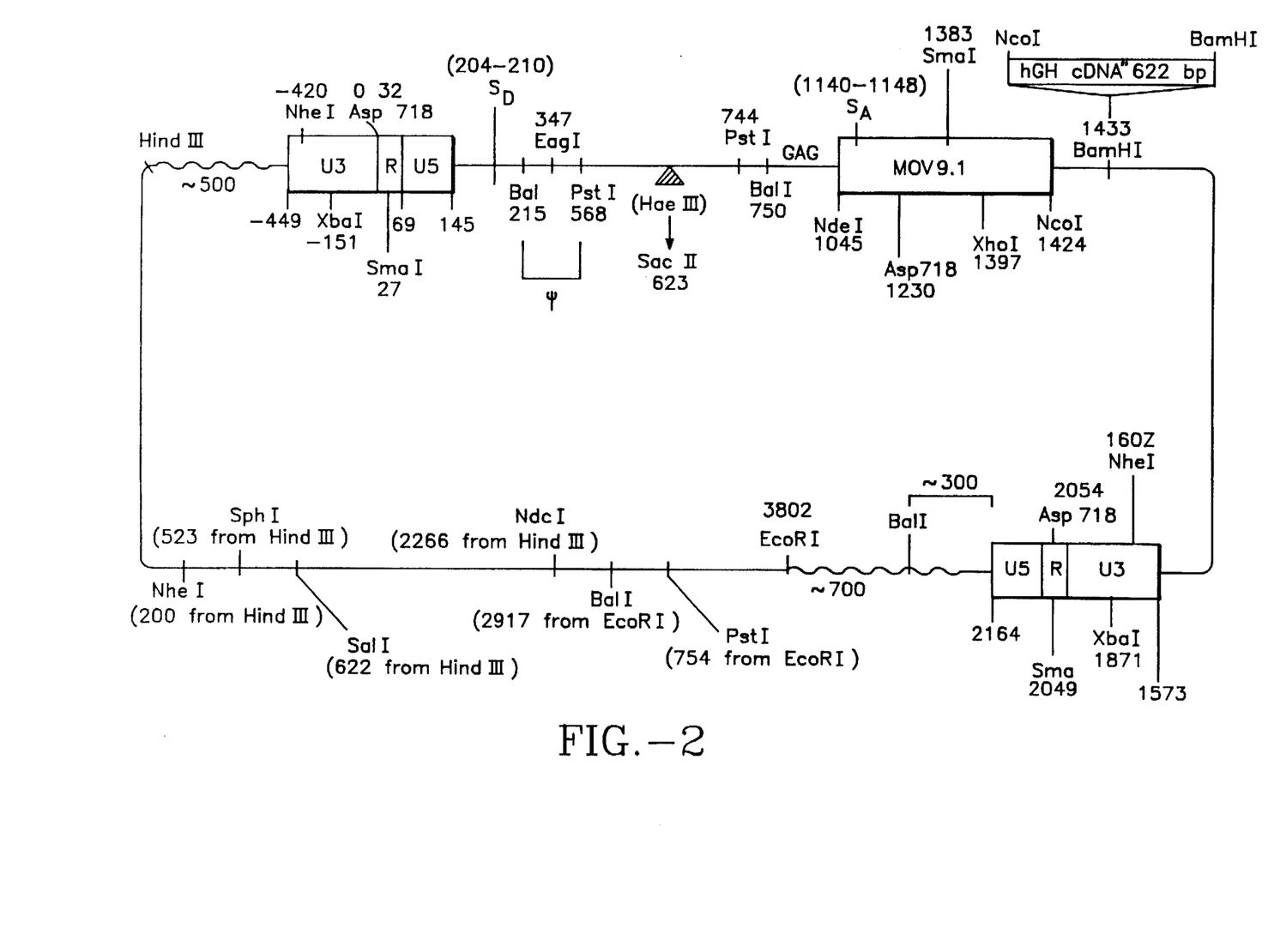
FIG. 2 is a map of the retroviral vector MFG.

(6) MFG (See FIG. 2) is a retrovirus that expresses the human growth hormone gene under the control of the viral LTR. The human growth hormone gene is inserted downstream of a fragment of the retroviral GAG gene. Splice donor and acceptor sites flank the ψ packaging sequence to allow splicing of the primary transcript and efficient generation of an hGH expressing mRNA. Splicing also leads to the removal of the ψ packaging sequence ensuring that the viral transcript cannot be used by endogenous retrovirus to form new infective virus in host cells. The producer cell line for this vector is ψCRIP, and known as S40.3.

(7) pE3TU is a plasmid that expresses the adeno E19 gene under the control of a CMV promoter and the neomycin resistance gene under the control of an SV40 promoter.

(8) pLXSN-E19 is a retrovirus that expresses the E19 gene under the control of the Moloney viral LTR and the neomycin resistance gene under the control of an SV40 promoter.

(9) pLXSH-E19 is a retrovirus that expresses the E19 gene under the control of the viral Moloney LTR and a hygromycin resistance gene under the control of an SV40 promoter.

pE3TU was constructed by inserting the 653 BamHI fragment of the adenovirus 2 gp 19 gene into the BamHI/HindIII sites in the polylinker of plasmid pCB6 (gift of D. Russell, M. Roth and C. Brewer). The adeno E19 fragment was obtained by digesting the d1712 plasmid (Bhat and Wold, (1987) *J. Virol.* 61:39–3945) which contains the adeno 2 E3 transcription unit cloned into the EcoRI site of pBR322. The parent retrovirus pLXSN was provided by A. D. Miller (Hock, et al., (1989) *Blood* 74:876–881).

pLXSN-E19 was constructed as follows. A ClaI/BamHI fragment of pE3TU was transferred into pBR322. The EcoRI-BamHI E19 containing fragment from the resultant plasmid was then ligated into the EcoRI-amHI sites of pLSXN retrovirus (MoMSV LTR).

pLXSH-E19 was constructed by removing the neomycin resistance gene with StuI and XbaI digestion and replacing it with a hygromycin gene isolated from pLHL (Palmer et al., *Proc. Natl. Acad. Sci. USA* (1987) 84:1055–1059).

The α-SGC and MFG retroviruses were generously provided to us by R. Mulligan and Somatix and the pE3TU plasmid and pLXSN-E19 and pLXSH-E19 retroviruses were generously provided by W. Wright (U. of Texas).

B. Evidence of migration of myoblasts in normal development

For this purpose, retroviral vectors were injected directly into muscle tissues. Genetic engineering occurred upon infection of dividing myogenic cells within muscle tissues. Viral stock (50–200 μl) was mixed with charcoal particles and 10 μM polybrene and injected from a 26 gauge needle into the laterodorsal surface of anesthetized Wistar rat hindlimbs. Animals were allowed to develop for about two weeks.

After 30–60 min lower hindlimbs were dissected free of skin, frozen in freezing isopentane and cut into serial 30 μm sections on a cryostat. Sections were post-fixed in 4% paraformaldehyde, washed and stained in 1 mg/ml X-gal, 5 mM potassium ferri- and ferrocyanide, 1 mM $MgCl_2$ in PBS overnight at 37° C., mounted in glycerol:PBS (9:1) and examined under bright field optics with a Zeiss Axiophot microscope for the presence of the blue X-gal reaction product. Clusters of muscle fibers stained blue were scattered throughout the lower hind limb. Charcoal particles were generally located between soleus and lateral gastrocnemius and were used to identify the site of infection. No differences in the distribution or size of clusters of labeled muscle cells were observed with either the BAG or MMuLVSVnlsLacZ vectors. The vectors were injected at various ages between day P9 (P=postnatal) and day P20 and analyzed between days P23–P37. In addition, clusters of labeled cells close to the charcoal particles were not detectably different from those several millimeters away, suggesting that the injection did not perturb development of nearby tissue.

Clusters of stained muscle fibers in the lateral gastrocnemius muscle demonstrated that the myoblasts could be infected and expressed β-galactosidase even after fusion into multinucleate fibers. Many of the clusters observed represented clones derived from single cells, some of the progeny of which migrated across basal lamina of a given muscle fiber and fused into adjacent muscle fibers. Since each myoblast is associated with a single fiber at the time of infection, the data indicate that myoblasts are capable of migrating through the basal lamina from one fiber to another. Moreover, since the majority (an average of 59% in seven experiments) of infection events yielded clones spanning multiple muscle fibers, migration appears to be a relatively frequent event.

To demonstrate that each cluster of β-galactosidase-positive cells in an infected rat leg originated clonally from a single retrovirally infected myoblast, a mixture of the two vectors was injected that generates distinct β-galactosidase staining patterns: nuclear and cytoplasmic. To maximize the number and size of clones, a mixture of the two vectors was injected into day P0 rat hindlimbs, a time when extensive proliferation and fiber formation is occurring. In two legs heavily infected with 87 separate β-galactosidase-positive clusters of which 23 contained cytoplasmic β-galactosidase, only in two instances did fibers adjacent to a cytoplasmically-stained fiber contain nuclear staining. Thus, the frequency with which adjacent myoblasts are infected independently is below 15% in animals infected at a level of 40–50 clones per lower hindlimb. Similar experiments in older animals with lower viral infection frequencies yielded clusters of labeled fibers marked with either nuclear or cytoplasmic β-galactosidase but not both. Thus, in the less heavily infected older hindlimbs, it is unlikely that any of the clusters derived from two or more separate infections. The vast majority are clones derived from a single infection event.

It is unlikely that new fibers formed during the period of the investigation, since the average number of fibers remained constant. In addition the mean diameter of fibers within clones was similar to the overall mean fiber diameter for the muscle. The data strongly support the migration of myoblasts through the basal lamina as the mechanism by which myoblasts are included in different fibers. See, Hughes and Blau (1990), supra.

The retroviral vector labelling technique has been used to demonstrate that in postnatal rodents individual myoblasts are not committed to forming particular populations of muscle fibers, for example fibers specialized for fast or slow contraction. Clones labelled by injection of MMuLVSVnlsLacZ contribute to all types of fibers in their environment. This finding suggests that a single clone of transfected myoblasts when injected into various muscles will be able to contribute to and participate in the regeneration of all types of muscle. (See also below.)

C. Evidence of migration of injected myoblasts into pre-existing myofibers at site of injection For this purpose, myogenic cells were marked (genetically engineered) in culture and subsequently injected into muscle tissues. Both the vectors LP328 and BAG were used for this purpose in order to determine whether a muscle-specific promoter such as HCA in LP328 would provide more stable long-term expression in muscle tissue than the viral MMuLV LTR in BAG. A permanent established mouse myogenic cell line, C2C12, was grown in Dulbecco's modified Eagle's medium and 15% calf serum and 5% fetal calf serum. The C2C12 myoblasts were either infected with BAG retrovirus (C2BAG) or cotransfected with a mixture of LP328 plasmid and a neomycin-resistance plasmid (C2ActLac) and grown in the presence of the neomycin analog G418. G418 resistant C2BAG or C2ActLac clones that expressed high levels of β-galactosidase based on staining with X-gal were subcloned and used in experiments.

Genetically engineered myoblasts were injected into mice (C3H male), twenty-six to thirty-two days of age. To provide the same environment for myoblasts containing different promoter constructs, both the right and left lateral gastrocnemii were injected. One gastrocnemius muscle of each mouse was injected with $5 \times 10^5$ C2BAG myoblasts in 10 μl PBS and the contralateral gastrocnemius muscle was injected with $5 \times 10^5$ C2ActLac myoblasts in 10 μl PBS. To mark the site of injection, charcoal was added to each cell suspension prior to injection.

To determine the time course of β-galactosidase expression in vivo, two mice were randomly selected and sacrificed at each time point: 10, 19, 40, 54, and 77 days after injection. For analysis, the legs were cut at the knee and the tibia removed. The lower leg was mounted in O.C.T. (Miles, Inc.) and quickly frozen in melting isopentane to −150° C. Each frozen block was serially sectioned into 30 μm sections. Sections were analyzed histochemically for β-galactosidase activity by X-gal staining and visualized by light microscopy.

Both types of myoblasts (C2BAG and C2ActLac) fused into pre-existing endogenous muscle fibers characterized by large fiber diameter. In addition, the myoblasts fused with other injected cells to generate new small diameter fibers. These were already apparent when legs were sectioned and stained for β-galactosidase activity at the earliest time point, 10 days after injection. Injected cells remained within the tissues and continued to express the foreign genes in muscle fibers of large fiber diameter for up to 180 days.

Injected myoblasts fused into muscle fibers of all types: specialized for fast or slow contraction. Single clones of mouse myoblasts, both permanent myogenic cell lines and primary mouse myoblast clones isolated from postnatal mouse hindlimb, were infected with LacZ-expressing retroviral vectors and returned to the legs of syngeneic mice by injection. The injected myoblasts fused into muscle fibers of all fiber types in all muscles tested, irrespective of the muscle of origin of the myoblasts or the nature of the target muscle. Moreover, the nature of the fibers to which the injected cells contributed were not altered by the procedure, even when the injected myoblasts expressed different myosin heavy chain isoforms in vitro from those expressed by the target muscle in vivo. These results suggest that single clones of myoblasts can be genetically engineered and once returned to the animal will contribute to all types of muscle fibers. Thus, a single modified human myoblast clone should be capable of contributing efficiently to fibers in any desired target human muscle.

D. Evidence of immune response to allogeneic myoblasts

Genetically engineered C2C12 cells (C2BAG) were injected into syngeneic, allogeneic, immunosuppressed or immunodeficient (scid) mice. As described above, injected myoblasts fused both with pre-existing endogenous muscle fibers and formed novel muscle fibers by fusing with one another. Injected myoblasts were maintained for the duration of the study (6 months) in the syngeneic C3H host (H-2$^k$). In contrast, cells were rapidly eliminated by 10 days after injection into allogeneic C57 mice (H-2$^b$). Daily i.p. injections of cyclosporine A (75 mg/kg but not 24 mg/kg) prevented this rapid loss and the cells were maintained during the 30 day treatment period and appeared comparable to cells in syngeneic or scid mice. During this time, the fibers containing injected myoblasts matured, as evidenced by the loss of fetal myosin heavy chain and H-2 of the donor haplotype. Two weeks after cyclosporine treatment was stopped, significant fiber loss and infiltration of the muscle by immune cells, primarily cytotoxic T-cells were observed. At 5 weeks, donor-containing fibers were scarce. These results show that because injected myoblasts fuse into pre-existing muscle fibers, transient immunosuppression targets healthy muscle for early destruction.

Further evidence that upon myoblast transfer, muscle precursor cells could be the target of rejection was obtained in studies with recombinant human interferon-gamma (r-H-IFN-γ). In these studies, we looked at MHC antigen expression after treatment with r-H-IFN-γ. FACS sorted human myoblasts were treated in vitro with r-H-IFN-γ and surface expression of HLA-DR, DQ, and DP was analyzed by flow cytometry and by PCR. All MHC Class II molecules were shown to be inducible by r-H-IFN-γ. These results point out that human myoblasts are able to express high levels of MHC Class II antigens when stimulated with interferon-65, a cytokine expressed in the course of graft rejection.

Other findings (Montegazza et al., (1991) *Neurobiology*, 41:1128–1132), in conjunction with the studies of injected allogeneic myoblasts, indicate that the use of allogeneic myoblasts in cell therapy of human muscle disorders, like other cell and organ transplants, requires either matching immunosuppression of patients, or some form of tolerization. Alternatively, myoblasts can be genetically engineered so that they escape immune surveillance.

E. Evidence of targeted migration of injected myoblasts to sites of muscle damage For this purpose, human myogenic cells were genetically engineered using replication defective retroviral vectors that encode LacZ (BAG and α-SGC) and subsequently injected into the muscle tissues of an mdx/scid mouse host. Mice doubly homozygous for the murine muscular dystrophy (mdx) and severe combined immunodeficiency (scid) mutations were specifically produced for these experiments to provide a convenient host for testing human myoblasts in the treatment of the human genetic muscle degenerative disorders, Duchenne muscular dystrophy (DMD) and Becker muscular dystrophy (BMD). The myopathy in these mice is characterized by foci of degeneration that develop in a number of different muscles. To assess the variables and optimize the conditions for introducing muscle cells into dystrophic muscle, the fate of individual muscle cells following injection into dystrophic mouse muscle was monitored by expression of β-galactosidase.

Primary human myoblasts are grown in Ham's F10, 10% fetal calf serum, 5% defined supplemented calf serum, 0.5% chick embryo extract, streptomycin sulfate (200 μg/ml) and penicillin G (200 units/ml). To maintain cells as replicating myoblasts, the cells are trypsinized when they reach 60–70% confluence and replated at a 1:4 dilution.

Human myoblasts are genetically engineered with either the BAG or the α-SGC retroviruses by collecting supernatant from retroviral producer cells. Producer cells are grown in high glucose Dulbecco's modified Eagle medium and 10% calf serum. To obtain supernatant for use in retroviral infection of human myoblasts the producer cells are plated at 2×10$^6$/100 mm dish. The next day, the medium is replaced with 10 ml of fresh medium. After 24 h, the medium is harvested, filtered through a 0.45 μm filter and 8 μg/ml polybrene is added. The medium is placed onto cultures of human myoblasts which are 20–30% confluent. The infection is performed overnight at 37° C., 10% $CO_2$. The medium containing the viral particles is aspirated and the cultures fed with fresh myoblast growth medium. The cells are grown for a minimum of 48 h before assaying for the expression of the gene of interest encoded by the retroviral construct. If the neomycin resistance gene is also encoded by the retroviral construct (e.g., BAG), the myoblasts are switched to growth medium containing 200–400 μg/ml G418 until resistant colonies form. The myoblasts are then labeled with antibodies to the cell surface protein N-CAM present on myogenic but not fibroblastic cell types and enriched to 95% using the fluorescence activated cell sorter.

Myoblasts are injected into muscle tissue and the site of injection is marked by inclusion of charcoal in the cell suspension. Two to 3.5 weeks after injection, the legs are collected, serial sectioned and analyzed for β-galactosidase labeled cells in different muscles. To identify the location of the genetically marked myoblasts, the tissues are first inspected with bright field optics at low magnification and then with Nomarski optics at high magnification for the blue staining provided by β-galactosidase with X-gal substrate.

The migration of human myoblasts in 10 mdx/scid legs is summarized as follows. Nine of the ten legs contained degenerating foci, the number per leg varying from 2–15. β-galactosidase expressing cells were found either at the site of injection or in the degenerating foci. As many as 58% of the foci in a leg contained β-galactosidase labeled cells. 50% of all labeled foci were on the opposite side of the leg. In contrast, in control scid/scid animals with no muscle degeneration, labeled myoblasts were only found at the site of injection.

F. Evidence of delivery of secreted, non-muscle gene products into the circulation by injection of genetically engineered myoblasts into muscle tissue To examine whether myoblasts could deliver non-muscle gene products to the circulation, we selected hGH for study. Sensitive assays distinguish mouse from human hormones and hGH has a short half-life of 4 minutes in serum, providing a stringent test for continuous production, secretion, and access to the circulation over time. To introduce the hGH gene into myoblasts, the MFG retroviral vector was used. The efficiency of stably introducing DNA into myoblasts by this approach is at least three orders of magnitude greater than by stable transfection of plasmids. Another vector, αSGC, was used to introduce the *E. coli* Lac Z gene which encodes β-galactosidase (β-gal) into the same myoblasts, providing an independent intracellular marker of implanted cell number and location. Recombinant MFG and α-SGC viruses were generated in the ψCRIP line that produces replication incompetent retrovirus with an amphotropic host range, allowing infection of mouse and human cells. Cells of the C2C12 mouse myogenic line were infected twice within 24 hours with a mixture of MFG and α-SGC retroviruses to create myoblast pool A. The efficiency of MFG infection was high: thirteen of fourteen (93%) randomly selected clones expressed and secreted hGH. The average rate of secretion for the pool was 4000 ng/$10^6$ cells/day, on a par with that of the most effective cell types in secreting recombinant hGH in vitro described to date.

Since some retroviral vectors cease to be expressed following cell differentiation or implantation, we examined whether transduced myoblasts continued to secrete hGH upon myotube formation in vitro. By several criteria hGH expressing myoblasts differentiated. The cells fused to form multinucleated myotubes. Northern analysis revealed the typical increase in transcripts for muscle α-actin, myosin heavy chain, and myosin light chain. Differentiation was accompanied by a change in the location of the Golgi apparatus in which hGH accumulated prior to secretion; in myoblasts it was polar and in myotubes it was characteristically circumnuclear. Despite these changes in differentiated state, the hGH secretion rate was not altered. Thus, although muscle is not generally considered to be a secretory tissue, both proliferating myoblasts and differentiated myotubes are capable of secreting hGH into the culture medium.

To determine whether transduced myoblasts could effectively deliver hGH in vitro, a single clone of myoblasts was injected into the hindlimbs of 12 mice. We selected clone 6 because it was the highest producer of hGH and because it also expressed β-gal, permitting the fate of injected cells to be monitored by histochemistry and by assay of tissue β-gal activity, as described below. At each designated time point, serum hGH was assayed by RIA. After an initial decline, serum hGH levels plateaued and persisted at approximately 0.5 ng/ml for 35 days. This level was significantly above that of control animals which were either uninjected or injected with cells expressing only β-gal. In a second series of experiments, a mixed population of transduced myoblasts, designated pool A, was injected into mouse hindlimbs to determine whether cells that had not been selected by clonal analysis could effectively deliver hGH to the circulation. Twenty-four mice were each injected with $10^{-7}$ myoblasts and monitored over time. The results were similar to those obtained with clone 6: after an initial decline, hGH levels persisted in serum at 1.0 ng/ml for a period of 30 days. These results show that hGH encoded by the MFG retrovirus can be continuously produced and secreted by myoblasts implanted into muscle tissue in vitro.

To monitor the fate of implanted cells, we used a highly sensitive fluorogenic assay of β-gal, (Roederer et al., *Methods in Enzymology* in press, 1991), a marker that is independent of the expression of the secreted protein hGH. β-gal activity was assayed for injected muscles and compared with a known number of transduced myoblasts in culture.

TABLE

| Experiment | Time after Myoblast Implantation (Days) | Serum hGH* (ng/ml) | Estimated Cell Number + (×$10^6$) |
|---|---|---|---|
| Pool A | 12 | 1.1 ± 0.5 | 2.8 ± 0.3 |
|  | 30 | 1.0 ± 0.6 | 3.5 ± 0.5 |
| Clone 6 | 14 | 0.8 ± 0.4 | 5.7 ± 1.5 |
|  | 35 | 0.4 ± 0.1 | 4.0 ± 1.1 |

Legend to Table: β-gal activity correlates with serum hGH and provides an estimate of cell number.

*Serum hGH (mean ± SD) was assayed as follows: hGH secretion was assayed by a solid phase two-site radioimmunoassay (Nichols Diagnostic Institute, San Juan Capistrano, California). Supernatant was collected after a 24 hour incubation, diluted 20-fold and assayed in duplicate. Standard curves were generated with purified hGH standards supplied by the manufacturer and drawn using second order polynomial interpolation.

+Cell number was estimated as a function of β-gal activity measured using a highly sensitive fluorogenic assay in which the nonfluorescent substrate 4-methyl umbelliferyl-β-D-galactoside (MUG) is cleaved specifically by β-galactosidase to produce the highly fluorescent product, 4-methyl umbelliferone. A standard curve was generated from known numbers of transduced myoblasts (either clone 6 or pool A) and cell number (mean±SEM) estimated from β-gal activity in injected muscles. As few as 25 Lac Z transduced cells could be detected. All assays were performed in duplicate. Extracts of muscle tissue were prepared by sonication (5×10 sec pulses at 4° C.) in 0.1M sodium phosphate pH 7.0 containing protease inhibitors (90 μg/ml PMSF, 0.2 units/ml aprotinin 0.1 mM leupeptin). Aliquots of tissue extract containing 10–20 μg protein were diluted 100 to 1000 fold in 0.1M sodium phosphate pH 7.0, 0.1% Triton X-100, 0.1M β-mercaptoethanol. The substrate (MUG; Sigma Chemical Co., St. Louis, Mo.) was added to a final concentration of 0.66 mM. After 30 minutes at RT the reaction was stopped by the addition of glycine-EDTA pH 11.2 to a final concentration of 120 mM glycine, 6 mM EDTA, and fluorescence generated by β-gal activity measured in a Fluoroskan microtiter plate reader (Flow Labs) using 355 nm excitation and 460 nm emission wavelengths. Control tissue samples from uninjected animals were consistently at least 30-fold below assays of injected animals.

Although this extrapolation is not precise, since it assumes that expression of β-gal in vivo and in vitro is similar, it is noteworthy that both in experiments with the cloned myoblasts and with the pool of myoblasts, the estimated number of cells required to deliver 0.5–1.0 ng/ml hGH to the serum approximated 4×$10^6$. As shown in the Table, for the pool and clone, respectively, the relative levels of β-gal activity paralleled values for serum hGH at different time points. These results suggest that the hGH concentration in serum at any given time is determined primarily by implanted cell number.

Tissue morphology was analyzed by histochemical analysis of β-gal distribution within hindlimbs injected either with myoblasts from a single clone or a pool at time points following myoblast implantation. Many β-gal labeled fibers have a relatively large diameter typical of the surrounding tissue, suggesting that implanted cells fused into and contributed to pre-existing myofibers.

Multiple small diameter fibers are also observed that are likely to be derived from implanted myoblasts that fused to one another. Although some labeled fibers have centrally located nuclei typical of regenerating muscle, in general the morphology of individual fibers and the architecture of the tissue as a whole were not greatly altered during the period of stable production of hGH.

Injected myoblasts of the C2C12 cell line appear to have three fates following implantation into mice; some are lost, some become integrated into fibers, and some proliferate. Four mice analyzed at late time points, days 56 and 85 after myoblast injection, had elevated serum hGH levels of 5.8±2.6 ng/ml and 16.1±10.1, respectively, and an abundance of mononucleated myoblast clusters. Proliferation appears to be a characteristic of the permanent C2C12 mouse myogenic cell line that is manifested months after implantation; it was not observed several months after primary mouse or primary human myoblasts were implanted in mice.

The experiments support that myoblasts are effective vehicles for long term deliver of secreted recombinant gene products. Injected genetically engineered myoblasts can be advantageous for this purpose because they are capable of fusing with mature muscle fibers and forming multinucleated heterokaryons in vivo. As an integral part of an endogenous structure, these injected cells have access to an extensive transcriptional and translational machinery, are in contact with the circulation and sustained by neuronal activity. Thus, implanted myoblasts are not only retained, but also nurtured.

That myoblasts persist is evidenced not only by their secretion of hGH but also by determining cell numbers based on β-gal activity. This finding is in marked contrast to most studies of recombinant gene delivery using other cell types in which circulating protein ceased to be detected. Although in some cases of recombinant gene delivery the basis for the lack of circulating protein was determined: extinction of vector expression, antibody degradation of the protein, lack of access to the circulation, or transplant rejection, in other cases it was not. The double labeling method presented here for assessing the fate of implanted cells complements the quantitative PCR used by others, by allowing the number, location, and morphology of injected cells to be monitored independent of the expression of the therapeutic gene product.

SUMMARY

It is evident from the above results that the subject invention allows for the use of muscle forming cells in the treatment of diseases associated with muscle tissue or for production of soluble or other proteins in a host. The myoblasts are capable of forming new muscle tissue or participating in the formation of fibers, where the cells may provide for useful properties, correct defects, and the like. In addition, the cells may be modified with markers, to allow for selective advantage of the transformed cells over the naturally present cells.

It is now found that myoblasts will migrate relatively far to damaged tissue, where the myoblasts may be injected into the damaged site or at adjacent tissue or may be introduced into the blood stream, particularly in a vessel feeding the damaged site and upstream from such site. The above results show that myoblasts may "home" to damaged sites, indicating a specific mechanism for the transfer of myoblasts to the damaged site for repair. In addition, when treating a patient, the myoblast cells may be modified to increase or decrease the expression or availability of surface membrane, cell adhesion molecules, MHC antigens, etc., to provide therapeutic amounts of native or foreign factors, e.g., growth factors, chemoattractants, or the like.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit of scope of the appended claims.

What is claimed is:

1. A method for producing a protein in muscle tissue in vivo as a result of the integration of DNA into myoblasts in culture, said method comprising:

injecting primary myoblasts into injured muscle tissue, wherein said myoblasts are substantially pure clonal cultures of at least five doublings, differ genomically from said muscle tissue as a result of introducing said DNA into said myoblasts, and are stably maintained;

whereby said myoblasts become integrated into said tissue and produce said protein, and expression of said protein is stably maintained.

2. A method according to claim 1, wherein said myoblasts have been transformed with a DNA construct comprising a replication-defective viral vector.

3. A method according to claim 1, wherein said protein is human growth hormone, and wherein said human growth hormone is secreted by said tissue.

4. A method according to claim 1, wherein said myoblasts are obtained from neonatal or adult tissue.

* * * * *

UNITED STATES PATENT AND TRADEMARK OFFICE
CERTIFICATE OF CORRECTION

PATENT NO. : 5,538,722

DATED : July 23, 1996

INVENTOR(S) : BLAU et al.

It is certified that error appears in the above-identified patent and that said Letters Patent is hereby corrected as shown below:

Column 1, line 10, in a new paragraph immediately preceding "INTRODUCTION", insert --This invention was made with Government support under Contract No. HD 18179 awarded by the National Institutes of Health. The Government has certain rights in this invention.--

Signed and Sealed this

Twentieth Day of January, 1998

Attest:

BRUCE LEHMAN

Attesting Officer

Commissioner of Patents and Trademarks